United States Patent [19]

Okajima et al.

[11] 4,389,523
[45] Jun. 21, 1983

[54] CELLULOSE SULFATE SALT HAVING ANTI-COAGULATING ACTION AND PROCESS FOR PREPARING SAME

[75] Inventors: Kunihiko Okajima, Takatsuki; Kenji Kamide, Ikoma; Toshihiko Matsui, Takatsuki, all of Japan

[73] Assignee: Asahi Kasei Kogyo Kabushiki Kaisha, Osaka, Japan

[21] Appl. No.: 324,918

[22] Filed: Nov. 25, 1981

[30] Foreign Application Priority Data

Nov. 27, 1980 [JP] Japan .................. 55-165786

[51] Int. Cl.$^3$ ............................................ C08G 18/10
[52] U.S. Cl. .................................... 536/59; 536/118; 536/122
[58] Field of Search ........................................... 536/59

[56] References Cited

U.S. PATENT DOCUMENTS

| | | | |
|---|---|---|---|
| 3,528,963 | 9/1970 | Reid | 536/59 |
| 3,609,377 | 9/1971 | Pettitt et al. | 536/59 |
| 3,624,069 | 11/1971 | Schweiger | 536/59 |
| 3,639,665 | 2/1972 | Schweiger | 536/59 |
| 4,064,342 | 12/1977 | Saika et al. | 536/59 |
| 4,141,746 | 2/1979 | Schweiger | 536/59 |

*Primary Examiner*—A. Lionel Clingman

[57] ABSTRACT

A cellulose sulfate salt having a heparinic action is provided, which satisfies requirements of $0.8 \leq <<F>> \leq 2.6$, $<<f_2>> \geq <<f_3>>$ and $<<f_2>> \geq <<f_6>>$ wherein $<<f_2>>$, $<<f_3>>$ and $<<f_6>>$ stand for probability of substitution of atoms H in the OH groups bonded to the $C_2$, $C_3$ and $C_6$ positions of the glucopyranose ring unit by sulfuric acid radicals, respectively, and $<<F>>$ stands for the total substitution degree which is the sum of $<<f_2>>$, $<<f_3>>$ and $<<f_6>>$. The cellulose sulfate salt is prepared by reacting a cellulose having a crystal form I with an $SO_3$/amine or $SO_3$/amide complex in an amount of 2 to 4 mole equivalents per glucose unit of the cellulose at $-10°$ C. to $40°$ C. to form a gelatinous product; adding water to the gelatinous product in an amount 0.1 to 5 times the amount of the starting cellulose used for the reaction; treating the mixture at a high temperature to relatively reduce the values of $<<f_6>>$ and $<<f_3>>$ among the values of $<<f_2>>$, $<<F_3>>$ and $<<f_6>>$; neutralizing, precipitating and drying the so obtained crude cellulose sulfate; dissolving the crude cellulose sulfate in water again; treating the solution with an adsorbent; and subjecting the treated cellulose sulfate to precipitation, drying, re-dissolution, dialysis, precipitation and then drying.

11 Claims, 1 Drawing Figure

CELLULOSE SULFATE SALT HAVING ANTI-COAGULATING ACTION AND PROCESS FOR PREPARING SAME

BACKGROUND OF THE INVENTION

(1) Field of the Invention

This invention relates to a cellulose sulfate salt which has heparinic properties, for example, a very high anti-coagulating property, and is useful as a substitute for natural heparin.

(2) Description of the Prior Art

Hemodialysis devices, hemodialysis membranes, hemodialysis hollow fibers and artificial blood vessels, which are used for treatment of patients of chronic renal insufficiency, are ordinarily surface-smoothened or treated with an anti-coagulant such as heparin so as to prevent coagulation of blood during an operation. In the case where hemodialysis is continued for a long time, when a blood vessel in the human body is connected to a dialysis circuit through a shunt, a physiological saline solution of heparin should be injected into the dialysis circuit so as to prevent coagulation of blood. External wounds, conditions after an operation of parturition, acute myocardial infarction, cardiac congestion, conditions of patients receiving the esterogene treatment (the treatment for prevention of pregnancy, milk secretion and menopausal disorder), gram-negative bacterium septicemia, polyglobulism, cetain protein deficiency and malignant tumors are exaggerated and complicated by venous thrombus. Recently, the heparin (anti-coagulant) treatment has attracted attentions as the method for preventing or mitigating these troubles. Persons having heritable disorders, such as anti-thrombin III deficiency and sickle-cell anemia, are liable to suffer from various thrombi. Furthermore, it is considered that the lung thrombus in a patient suffering from cancer is often a prodrome of death. Recently, anti-coagulants have been used for the treatment of these various thrombi. Moreover, it is said that anti-coagulants such as heparin have an action of curing lipemia or an activity of inhibiting various enzymatic actions.

Heparin is present in animal organs, such as the lungs, kidney and liver. Accordingly, the extraction of heparin from these organs and the purification of the extracted crude heparin are very troublesome, and the manufacturing cost is high. Moreover, it is very difficult to obtain heparin products having the same structure and capacity from different organs.

Many attempts have heretofore been made to synthesize substitutes for natural heparin, and as typical instances of such synthetic substitutes, there can be mentioned a polyvinyl alcohol sulfate ester and a polysaccharide sulfate ester. In 1935, S. Bergstöm first reported that the latter sulfate ester has a heparinic activity [see Natur Wissenschaften, 25, 706 (1935)]. The reported polysaccharide sulfate ester includes chondroitin sulfate, chitin sulfate, pectic sulfate, starch sulfate and cellulose sulfate. It is taught that chlorosulfuric acid and pyridine were used for esterification of cellulose with sulfuric acid, but none of the molecular weight, the distribution of the substitution degree and other molecular characteristics are described. Afterward, A. Astrup et al revealed that cellulose sulfate esters have an anti-coagulating property [see Acta Physiol. Scand., 8, 215 (1944) and ibid, 9, 351 (1945)]. A. Astrup et al obtained a cellulose sulfate triester (the total substitution degree (F) is approximately 3.0) by using a chlorosulfuric acid-/α-pyrroline complex as an esterifying agent, but influences of the molecular weight and molecular characteristics of the cellulose sulfate ester were not taught at all by A. Astrup et al. In each of these known methods of producing cellulose sulfate, highly toxic and highly corrosive chlorosulfuric acid is used, and these known methods cannot be made fit for practical use. Moreover, there is a risk of incorporating the highly toxic chlorosulfuric acid ions into the product, and therefore, the product cannot be used as an anti-coagulant from the viewpoint of safety. Still further, the sulfate ester having a high substitution degree [(F) is approximately 3.0] is poor in storage stability and cannot be stored for a long time in bulk or solution form, and therefore, it is not valuable as a medicine.

The influences of the distribution of the substitution degree, the molecular weight and the molecular characteristics on the anti-coagulating property of the above-mentioned cellulose sulfate esters are important. The distribution of the substitution degree is especially significant. By the term "distribution of the substitution degree" used herein is meant a proportion of the substituents, with which hydrogen atoms in the OH groups bonded to the $C_2$, $C_3$ and $C_6$ positions of the glucopyranose ring have been substituted, to the total hydrogen atoms in the OH groups bonded to the $C_2$, $C_3$ and $C_6$ positions. Ordinarily, a polymeric substance is a mixture of molecules differing in the degree of polymerization. Accordingly, the above-mentioned distribution of the substitution degree is a double mean value, and the value is designated as $<<f_k>>$ ($k=2, 3, 6$) in the present specification. The average substitution degree $DS[=<<F>>]$ heretofore used is represented by the formula: $DS=<<F>>=<<f_2>>+<<f_3>>+<<f_6>>$. Characteristics of cellulose derivatives have heretofore been evaluated based on DS ($=<<F>>$) alone. However, the distribution of the substitution degree is very significant to the anti-coagulating property. This will readily be understood from the fact that the anti-coagulating property of natural heparin is lost if the sulfonyl group is removed from the aminosulfonyl group present as a substituent at the $C_2$ (the second carbon atom) position of the uronic acid ring as the constituent unit of natural heparin.

Figure 1:
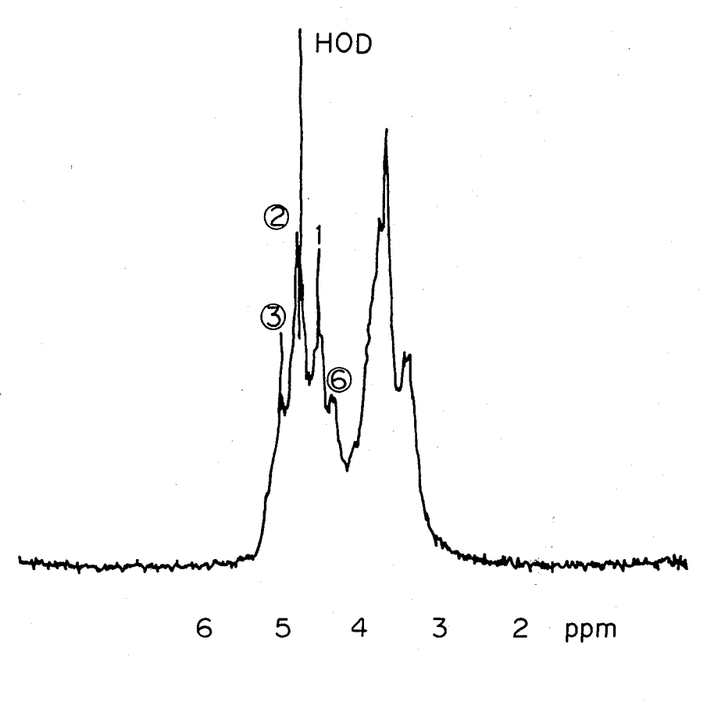
The accompanying drawing shows a pulse Fourier transform $H^1$-NMR diagram of sodium cellulose sulfate [$<<F>> = 1.96$] in heavy water, in which 1,②③and ⑥indicate peaks of protons bonded to the $C_1$ position and sulfuric acid residues substituted $C_2$, $C_3$ and $C_6$ positions, respectively.

The above-mentioned values $<<F>>$ and $<f_k>>$ can be determined by chemical analysis and $H^1$-NMR or $H^1$-NMR alone. Only $<<F>>$ can be determined by chemical analysis. More specifically, a cellulose sulfate salt is decomposed by hydrochloric acid, barium chloride is added to the decomposition product and the value $<<F>>$ is calculated as barium sulfate according to the weight method. The values $<<f_k>>$ can be determined by $H^1$-NMR according to the following formulae:

$$<<f_2>> = \frac{7I_2}{\sum_{i=1}^{6} I_i}, <<f_3>> = \frac{7I_1}{\sum_{i=1}^{6} I_i} \text{ and}$$

$$<<f_6>> = <<F>>^* - [<<f_2>> + <<f_3>>] \text{ or}$$

$$<<f_6>> = \frac{7I_4/2}{\sum_{i=1}^{6} I_i^{**}}$$

*Value determined according to chemical analysis
**$I_i$ ($i = 0\ 1 \sim 6$) indicates the peak intensities at 4.97, 4.83, 4.56, 4.39, 4.0–3.5 and 3.42 ppm in the accompanying drawings, wherein there is shown an $H^1$—NMR spectrum diagram of sodium cellulose sulfate of the present invention in heavy water.

Furthermore, it should naturally be expected that the anti-coagulating property will be influenced by the molecular weight and the molecular weight will also have influences on the fundus membrane permeability of the cellulose sulfate salt.

SUMMARY OF THE INVENTION

It is a primary object of the present invention to provide a cellulose sulfate salt, as a substitute for natural heparin, which is comparable or superior to natural heparin in heparinic properties such as the anti-coagulating property, is homogeneous in quality, and can be prepared stably with economical advantages.

In accordance with the present invention, there is provided a cellulose sulfate salt having a heparinic action, which satisfies the requirements of $0.8 \leq <<F>> \leq 2.6$, $<<f_2>> \geq <<f_3>>$ and $<<f_2>> \geq <<f_6>>$ wherein $<<f_2>>$, $<<f_3>>$ and $<<f_6>>$ stand for probability of substitution of atoms H in OH groups bonded to the $C_2$, $C_3$ and $C_6$ positions of the glucopyranose ring unit by sulfuric acid residues, respectively, and $<<F>>$ stands for the total substitution degree $[= <<f_2>> + <<f_3>> + <<f_6>>]$.

DESCRIPTION OF THE PREFERRED EMBODIMENTS

The cellulose sulfate salt of the present invention has a total average substitution degree $<<F>>$ of from 0.8 to 2.6.

A cellulose sulfate salt having a value $<<F>>$ exceeding 2.6 has a sufficient anti-coagulating action but the salt involves problems concerning long-period maintenance of the anti-coagulating property and the stability quality. For example, when a physiological saline solution of a cellulose sulfate salt characterized by $<<F>> = 2.80$, $<<f_2>> = 1.00$ and $<<f_6>> = 0.90$ is stored for a long time, both the pH value and the viscosity of the solution tend to decrease, as described in the specification of U.S. Pat. No. 3,609,377. This U.S. patent specification teaches, as means for avoiding this disadvantage, a method in which a powder of an alkali metal salt of a weak inorganic acid is added. However, from the viewpoint of the primary object of the present invention, that is, provision of a cellulose sulfate salt suitable as a medicine, this method is not preferred, and no substantial solution of the problem can be obtained by this method. Furthermore, the anti-coagulating property is drastically reduced simultaneously with the above-mentioned decrease of the pH value and viscosity. In contrast, a cellulose sulfate salt having a value $<<F>>$ smaller than 0.80 does not show a high anti-coagulating property. In view of the preparation process described hereinafter, it is preferred that the value F be in the range of $1.5 < <<F>> < 2.4$. In connection with the relation among $<<f_2>>$, $<<f_3>>$ and $<<f_6>>$, if the value $<<F>>$ is in the above-mentioned preferred range of $1.5 < <<F>> < 2.4$, the value $<<f_2>>$ should preferably be about 1.00. This preferred value of $<<f_2>>$ coincides with the fact that if the aminosulfonyl group bonded to $C_2$ of heparin is cut off, the anti-coagulating property of heparin is lost. In the range of $0.8 \leq <<F>> \geq 2.6$, an increase of the value $<<F>>$ results in an increase of the anti-coagulating property. However, in the range of $1.5 < <<F>> < 2.4$, if the value $<<f_2>>$ is about 1.00, the anti-coagulating property is substantially constant and this anti-coagulating property is stable even if the cellulose sulfate salt is stored for a long time. Also from this fact, it is preferred that the value $<<F>>$ be in the range of $1.5 < <<F>> < 2.4$.

The influences of the relation between the sulfate substitution degree $<<F>>$ and the limiting viscosity number $[\eta]$ (as determined as sodium sulfate at 25° C. in a 0.5 N aqueous solution of sodium sulfate) on the anti-coagulating property are complicated. In order to obtain a substantially constant high anti-coagulating property, for example, in the case of $<<F>> = 1.69$, a cellulose sulfate having $[\eta]$ of 10 to 66 is effective, in the case of $<<F>> = 1.94$, a cellulose sulfate having $[\eta]$ of not more than 112 is effective and in the case of $<<F>> = 2.60$, a cellulose sulfate having $[\eta]$ of lower than 430 is effective. It is ordinarily preferred that the value $[\eta]$ be in the range of $10 < [\eta] < 430$. If the value $[\eta]$ is larger than 430, the molecular weight is too high and the cellulose sulfate salt involves a problem concerning the fundus membrane permeability in the living body. If the value $[\eta]$ is smaller than 10, separation of the intended product becomes difficult in the preparation process and industrial synthesis becomes difficult. For these reasons, it is preferred that the value $[\eta]$ be in the above-mentioned range. With the reduction of the value $<<F>>$, the lower limit of the value $[\eta]$ of the cellulose sulfate salt critical for obtaining an effective anti-coagulating property is reduced.

Another characteristic value specifying the cellulose sulfate salt of the present invention is the index a defined by the following two relative formulae of the limiting viscosity number $[\eta]$ to the number average molecular weight Mn and the weight average molecular weight Mw:

$$[\eta] = K_1 \times Mn^1 \text{ and}$$

$$[\eta] = K_2 \times Mw^a$$

wherein $K_1$ and $K_2$ are constants.

Ordinarily, the value a indicates the expansion of the polymer chain in a solution. It is said that the larger the value a, the higher the draining effect and the larger the expansion of the polymer chain. When the expansion of the polymer chain is large, the action (i.e., the contact probability) of the polymer on other substances per unit volume increases. In the cellulose sulfate salt of the present invention, the index a is not less than 0.9. For example, in the case of a cellulose sulfate salt characterized by $<<F>> = 1.96$, $<<f_2>> = 1.00$, $<<f_3>> = 0.61$ and $<<f_6>> = 0.35$, the index a is 0.98 or 0.97 as indicated by the following formula:

$$[\eta] = 7.19 \times Mw^{0.98} \text{ or } [\eta] = 1.65 \times Mn^{0.97}$$

As the cellulose sulfate salts of the present invention, there can be mentioned sodium, calcium, magnesium and barium salts. Among these salts, the sodium salt is most preferred from the viewpoints of the anti-coagulating property and solubility. The potassium and barium salts are extremely poor in water solubility, but these salts can satisfactorily be used when water solubility is not especially required.

Cellulose sulfate salts can be prepared according to the following procedures.

Cellulose is sulfated and then neutralized with sodium hydroxide, calcium oxide or potassium hydroxide to form a cellulose sulfate salt. Furthermore, a cellulose sulfate salt may be obtained by treating the sulfate salt obtained by the above neutralization with an aqueous solution of an alkali metal or alkaline earth metal salt such as potassium chloride, magnesium chloride, calcium chloride, barium chloride or sodium chloride. Various processes for sulfation of cellulose are known. For example, there can be mentioned a process using a mixed liquid of concentrated sulfuric acid and alcohol as an esterifying agent (hereinafter referred to as "process I"), a process using a mixed liquid of chlorosulfuric acid and amine as an esterifying agent (hereinafter referred to as "process II") and a process using a sulfur trioxide/amide complex or a sulfur trioxide/amine complex as an esterifying agent (hereinafter referred to as "process III").

The substitution degree $<<F>>$ of the cellulose sulfate obtained according to the process I is about 1.00 at the highest, and it is impossible to make the value $<<F_2>>$ largest among the values $<<f_2>>$, $<<f_3>>$ and $<<f_6>>$, which is an indispensable requirement of the present invention as pointed out hereinbefore. Therefore, the cellulose sulfate salt of the present invention cannot be obtained according to the process I. Moreover, in this process, extraordinary labor and cost are necessary for purifying the obtained cellulose sulfate salt. The process II is suitable for obtaining a product having a value $<<F>>$ of about 3.00, and the cellulose sulfate salt obtained according to this process have a very high anti-coagulating property in the as-prepared state. However, from the experiments made by us, it was confirmed that, if this cellulose sulfate salt having a value $<<F>>$ of about 3.00 is stored for a long time, for example, 3 months, the anti-coagulating property is drastically reduced. In connection with the relation between $<<F>>$ and $<<f_k>>$ (k=2, 3, 6), it also was found that the value $<<F>>$ is 1.52 and the relation of $<<f_3>>$ > $<<f_2>>$ ≈ $<<f_6>>$ is established. That is, it was confirmed that the value $<<F>>$ is reduced and the value $<<f_2>>$ is not largest among the values $<<f_2>>$, $<<f_3>>$ and $<<f_6>>$. Accordingly, the process II is disadvantageous in that the stability of the obtained cellulose sulfate salt with the lapse of time is not satisfactory and also in that if the sulfuric acid substituent is cut off by some means or other, a cellulose sulfate salt satisfying the requirement that the value $<<f_2>>$ is largest among the values $<<f_2>>$, $<<f_3>>$ and $<<f_6>>$ cannot be obtained. Moreover, this process is not suitable for the production of a medicine, because chlorosulfuric acid having a high toxicity is used. In principle, the cellulose sulfate salt of the present invention is prepared according to the process III. This process is outlined in the specification of U.S. Pat. No. 3,624,069, but conditions for preparing sulfates having a heparinic action are not disclosed at all. The process III is characterized in that the process comprises the step of partially de-esterifying a cellulose sulfate in sulfating cellulose with a sulfur trioxide/amine complex or sulfur trioxide/amide complex, so that the value $<<f_2>>$ is largest among the values $<<f_2>>$, $<<f_3>>$ and $<<f_6>>$, and the step of subjecting the crude cellulose sulfate salt to a treatment with an adsorbent to remove impurities as much as possible, so that the resulting product can be used in the field of medicines. More specifically, the process for preparing the cellulose sulfate salt of the present invention comprises: the step of mixing cellulose with a wetted sulfur trioxide/amide complex (1 mole/2 moles) or a wetted sulfur trioxide/amine complex (1 mole/2 moles) in an amount of 2 to 4 moles per glucose unit of the cellulose and subjecting the mixture to sulfation at a temperature of from $-10°$ C. to $40°$ C.; the step of adding water in an amount 0.1 to 5 times the amount of the starting cellulose to the reaction product to control the distribution of the sulfuric acid substitution; the step of neutralizing the reaction product with an alkali; the step of precipitating the neutralization product with an alcohol to obtain a crude precipitate, the step of roughly washing the crude precipitate, the step of dissolving the crude precipitate in water again and subjecting the solution to a treatment with an adsorbent, the step of re-precipitating, re-dissolving and dialyzing the adsorbed precipitate, and the step of recovering a purified cellulose sulfate salt by precipitation or evaporation.

The process for preparing the cellulose sulfate salt of the present invention will now be described in detail.

Cellulose that can be used in the present invention is limited to natural cellulose, and only cellulose having a crystal form I can be used. Celluloses having other crystal forms, for example, rayon (crystal form II) and cupra (crystal form III), cannot be used in the present invention, because products having a value $<<F>>$ not smaller than 1.00 cannot be obtained from these celluloses. Cellulose (crystal form I) in which the molecular weight has been adjusted by hydrolysis or the like may be used in the preparation process.

As the amines and amides which are used for the preparation of the sulfur trioxide/amine complex or sulfur trioxide/amide complex used as the esterifying agent, there can be mentioned, for example, tertiary amines such as pyridine (Py), picoline (Pyc), quinoline (Qui), triethylamine (TEA), tributylamine (TBA) and tripropylamine (TPA), and amides such as N,N'-dimethylformamide (DMF), N,N'-dimethylacetamide (DMAc), acetamide (AA), N-monomethylformamide (MMFA) and N-monomethylacetamide (MMAc). From the viewpoints of cost of the solvent, the ease with which a complex with sulfur trioxide can be formed and the stability of the complex, dimethylformamide and pyridine are preferred among these amines and amides. If the reactivity with cellulose is not considered, then a sulfur trioxide/dioxane complex may be used. Ordinarily, these complexes are white solids having a composition of 1 mole/1 mole, and since these solids cannot conveniently be used for the reaction with cellulose, they are ordinarily used in the state wetted with the amine or amide constituting the complex (for example, 1 mole of the complex is wetted with 1 mole of the amine or amide). Cellulose may be swollen with an amine, an amide or a sulfoxide prior to the reaction with such complex. In this case, use of the same solvent as the solvent constituting the complex is advantageous from the viewpoint of the ease with which separation and purification take place after the reaction or in the operation at other steps. The amount of the solvent used for swelling the cellulose is ordinarily 1 to 5 times the amount (weight) of the cellulose, and if the solvent is used in a larger amount, no particular increase of the effect is attained and the process becomes economically disadvantageous because of higher cost for the solvent recovery. Of course, the cellulose may be reacted with a sulfur trioxide ($SO_3$)/amine or amide complex (1 mole/2 moles) without the addition of the swelling solvent prior to reaction. Such solvent may be added during the reaction. Also in this case, it is sufficient to use the solvent in an amount 1 to 5 times the amount (weight) of the cellulose.

When the amount of the wet complex consisting of 1 mole of sulfur trioxide and 2 moles of the amine or amide is regarded as being 1 mole, the wet complex should be reacted with cellulose in an amount of 2 to 4 moles per mole of the glucose residue of the cellulose. If the amount of the complex is smaller than 2 moles, when a solution is prepared by the addition of water after completion of the reaction, undesirable floating of the unreacted cellulose becomes conspicuous. In contrast, if the complex is used in an amount exceeding 4 moles, the reaction with cellulose is theoretically accelerated, but the ratio of effective utilization of the chemical is reduced and when a homogeneous solution is prepared to control the degree of substitution after completion of the reaction, the relation of $<<f_3>>><<f_2>>\geq<<f_6>>$ is often established.

The reaction temperature is in the range of from $-10°$ C. to $40°$ C. Since the reaction is exothermic, it is preferred that the reaction be carried out at a temperature lower than room temperature. The reaction is ordinarily completed within 1 to 4 hours.

The first characteristic feature of the preparation process of the present invention resides in the step of forming a cellulose sulfate salt which satisfies the experimentally established conditions of $<<f_2>>\geq<<f_3>>$ and $<<f_2>>\geq<<f_6>>$ necessary for obtaining an excellent anti-coagulating property with a good storage stability when the value $<<F>>$ is in the range of $0.8\leq<<F>>\leq 2.6$, especially $1.5<<<F>><2.4$. This characteristic step is the step of adding water to the reaction product and treating the resulting mixture at a predetermined temperature. Positive addition of water to the reaction mixture during the course of preparation of cellulose sulfate is denied in the specification of U.S. Pat. No. 3,624,069 because it is considered that this positive addition of water results in reduction of the reaction efficiency of the sulfur trioxide/amide complex. On the other hand, the specification of U.S. Pat. No. 3,639,665 teaches that in the process of sulfation of cellulose with a sulfur trioxide/amide complex, the presence of water in an amount of up to 10% by weight based on the cellulose is effective at the step of presoaking the cellulose. In this process, water is already present before initiation of the heterogeneous sulfation reaction. This means that a small amount of sulfuric acid is always present in the system at the start of sulfation with the sulfur trioxide/amide complex. In this case, certain changes can be given to the reactivity at the $C_2$, $C_3$ and $C_6$ positions of cellulose, but the requirement of the present invention that the value $<<f_2>>$ should be largest among the values $<<f_2>>$, $<<f_3>>$ and $<<f_6>>$ can hardly be satisfied. In the present invention, water is added to sulfated cellulose. That is, in the process of the present invention, water is added after the distribution of $<<f_2>>$, $<<f_3>>$ and $<<f_6>>$ has once been established, and control of the substitution degree is mainly accomplished by hydrolysis of the sulfuric acid groups pending on the side chains. The substantial difference between the process disclosed in the specification of U.S. Pat. No. 3,639,665 and the process of the present invention resides in whether water is added at the time of reaction or at the time of reverse reaction. The cellulose chemistry teaches that if the order of reactivity of the reactant to the positions $C_2$, $C_3$ and $C_6$ in a normal reaction is of $C_2<C_3<C_6$, the order is reversed in a reverse reaction (substituent-removing reaction in this case). Therefore, it is very difficult to obtain the cellulose sulfate salt of the present invention according to the process disclosed in the specification of U.S. Pat. No. 3,639,665. In other words, as the result of various examinations made on sulfation of cellulose, it has been found that when a sulfur trioxide type complex is used, a cellulose sulfate satisfying the above requirement can be obtained by a very simple method of adding water to sulfated cellulose.

Good results are ordinarily obtained if water is added to sulfated cellulose in an amount 0.1 to 5 times the amount of the starting cellulose. The resulting solution is treated at a temperature of not higher than $60°$ C. for 3 to 45 minutes. The amount of water added should be determined relative to other conditions such as the temperature and treatment time. Ordinarily, if the amount of water is smaller than 0.1 time the amount of the starting cellulose, the degree of sulfation of the remaining $SO_3$ complex is very low and the dissociation characteristic of the sulfuric acid residues substituted on cellulose is undesirably reduced. When water is added in an amount larger than 5 times the amount of the starting cellulose, the degree of sulfation of the $SO_3$ complex and the dissociation characteristic of the substituted sulfuric acid radicals are high, but these become too high and it becomes difficult to set temperature and time conditions suitable for controlling the substitution degree. Moreover, if a large amount of water is present in the reaction mixture, the efficiency of recovery or re-utilization of the solvent is reduced. Of course, the temperature and time conditions have relations to the composition at the point of termination of the reaction, the degree of the sulfuric acid substitution (it may be considered that when a sulfur trioxide complex is added in an amount larger than 3 moles per mole of cellulose, the value $<<F>>$ is ordinarily 2.0 or more) and the value $<<F>>$ of the cellulose sulfate salt finally adjusted by the addition of water. For example, when water is added to a reaction product obtained by using a sulfur trioxide/dimethylformamide (1 mole/2 moles) complex in an amount of 3 moles per mole of cellulose, in an amount 2 times the amount (weight) of the starting cellulose, and the resulting solution is heated at $60°$ C. for 5 minutes, neutralized with sodium hydroxide and precipitated with methanol, there is obtained sodium cellulose sulfate characterized by $<<F>>$ of 1.87, $<<f_2>>$ of 0.90, $<<f_3>>$ of 0.70 and $<<f_6>>$ of 0.27. When water is added to the above-mentioned reaction product in an amount 5 times the amount of the starting celluloe and the resulting solution is allowed to stand still at room temperature for 20 minutes, neutralized with sodium hydroxide and precipitated with methanol, there is obtained sodium cellulose sulfate characterized by $<<F>>$ of 2.12, $<<f_2>>$ of 0.92, $<<f_3>>$ of 0.72 and $<<f_6>>$ of 0.48. On the other hand, when the above-mentioned reaction product is directly neutralized with sodium hydroxide and precipitated with methanol, there can be obtain a product having smaller values of $<<F>>$ and $<<f_2>>$, that is, a product characterized by $<<F>>$ of 1.67, $<<f_3>>$ of 0.68, $<<f_2>>$ of 0.55 and $<<f_6>>$ of 0.54.

The solution obtained by the addition of water and the use of a heat treatment is neutralized with an aqueous solution or an alcoholic aqueous solution of sodium hydroxide, potassium hydroxide, calcium hydroxide or lithium hydroxide. At this neutralization step, the alkali concentration is not particularly critical, but when a dilute alkali solution is used, there can be attained an effect of reducing the particle size of the cellulose sulfate salt obtained at the subsequent precipitation step. It is preferred that neutralization be carried out under a slightly alkali-excessive condition so that the pH value of the solution is about 8 to about 9. The reason is that complete conversion of the sulfuric acid residue substituted on cellulose to a salt can definitely be effected if such condition is adopted. If a trace amount of the sulfuric acid residue is bonded to cellulose in the form of a free acid, when an aqueous solution of this cellulose sulfate salt is stored, the substituents are self-decomposed and the anti-coagulating property is reduced. It is expected that this tendency of removal of the substituent will be most prominent at the position $C_6$.

At the precipitation step, alcohols, ketones and ethers may be used as the precipitating agent. Use of methanol is preferred from the economical viewpoint. As the method of using the precipitating agent, there may be adopted a method in which the neutralized solution is added to a large amount of the precipitating agent and the mixture is stirred and a method in which the precipitating agent is added to the neutralized solution. The obtained precipitate is recovered by filtration and it is preferred that the recovered precipitate be washed with a methanol/water mixed liquid repeatedly. This washing treatment is effective for shortening the times required for the subsequent absorption and dialysis treatments.

In order for the obtained product to be used as a medicine, it is necessary to remove impurities therefrom as much as possible. If pyrogenic substances such as amides are contained in the product, it often happens that the product cannot pass the pyrogenic test. The second important characteristic feature of the process of the present invention is that amides and amines can be removed from the product very effectively. Ordinarily, the cellulose sulfate salt obtained according to the above-mentioned procedures is extremely contaminated with amides and amines and the dry product has a pale brownish color. An aqueous solution of such a product is ordinarily brown. There is a risk that such a product cannot be used as a medicine or in other fields. In order to obviate this risk, it is necessary to repeat the cycle of the steps of dissolution, precipitation, drying, re-dissolution and re-precipitation from several times to scores of times. We made researches with a view to simplifying this complicated refining process and found that when an aqueous solution of the crude cellulose sulfate salt is treated with an adsorbent such as diatomaceous earth, active carbon, a metal oxide or a metal hydroxide, the refining process can surprisingly be shortened and simplified. By this treatment, not only impurities inevitably included in the product but also low-molecular-weight impurities included in the course of the preparation can be removed. The adsorption treatment of the aqueous crude cellulose sulfate should preferably be carried out to an extent such that the nitrogen content in the finally obtained cellulose sulfate salt is not more than 0.01% by weight. As the adsorbent that can be used in the present invention, there can be mentioned diatomaceous earth, activated alumina, montmorillonite, kaolin, zirconium oxide, zirconium hydroxide, titanium oxide, titanium hydroxide, asbestos and active carbon. From the economical viewpoint and in view of the ease with which filtration of the aqueous solution of the cellulose sulfate salt can be accomplished, diatomaceous earth and active carbon are preferred. The amount of the adsorbent to be added to the aqueous solution of the cellulose sulfate salt is not particularly critical. If the amount of the adsorbent is increased, the subsequent steps can accordingly be simplified. However, an appropriate amount of the adsorbent should be determined while taking economical factors and the like into consideration. When the treatment is conducted batchwise, satisfactory results can ordinarily be obtained if the adsorbent is used in an amount of 0.1 to 0.6 g per gram of the crude cellulose sulfate salt. The treatment may be accomplished by adding the adsorbent to the aqueous solution of the cellulose sulfate salt, allowing the mixture to stand still for 10 to 60 minutes and carrying out filtration, or by passing the aqueous solution of the cellulose sulfate salt through a column packed with the adsorbent. The adsorbent used for the treatment may be regenerated by an acid or alkali treatment and then used for the treatment again. The solution which has thus been treated with the adsorbent is substantially colorless and transparent, and the cellulose sulfate salt precipitated from this solution is white. The pH value of the so obtained aqueous solution of the cellulose sulfate salt is in the range of from 5.3 to 7.0 as determined at a concentration of 5 g/dl, though the pH value is changed to some extent according to the degree of absorption of carbon dioxide gas from air.

Then, the cellulose sulfate salt is dissolved in deionized water again and dialyzed. Various membranes may be used as the semipermeable membrane for the dialysis, but ordinarily, satisfactory results are obtained by use of a collodion membrane. The dialysis should be carried out so that when the resulting cellulose sulfate salt is dissolved in deionized water at a concentration of 5 g/dl, the specific electric conductivity of deionized water (having a specific electric conductivity of $10^{-7}$ to $10^{-8} \Omega^{-1}$ cm$^{-1}$) used as the dialyzing liquid is not higher than $10^{-5} \Omega^{-1}$ cm$^{-1}$ after the dialysis. If this condition is not satisfied, amounts of free ions (mainly sulfuric anions and sodium cations) contained in the cellulose sulfate salt cannot be neglected. Although the residual free ions have no substantial influences on the anti-coagulating property, in view of the high purity required for a medicine, these free ions should be removed as much as possible.

The anti-coagulating property of the so obtained cellulose sulfate salt may be evaluated according to various methods. In the present specification, the anti-coagulating property is evaluated according to the Lee-White method and the Imai method. The former method is qualitative and the latter method is quantitative. Commercially available heparin (152 IU/mg) is used as a reference sample. In the Lee-White method, a nip-mouth injector having a capacity of 3 ml is used, and the inner wall of the injector is washed with 2 ml of a physiological saline solution and the washing solution is ejected from the injector. Then, 1.0 ml of a 0.01% (weight/volume) solution of a cellulose sulfate salt and 1.0 ml of a 0.01% (weight/volume) solution of heparin, both in a physiological saline solution, are sucked into the injector and the inner wall is sufficiently washed and the solution is ejected from the injector by pressing with a finger. Then, 1.00 ml of fresh blood collected from the human body (hereinafter referred to as "whole blood") is charged into each injector treated with the sample solutions and an injector (blank) treated with the physiological solution alone, and the time of initiation of coagulation is carefully determined. Furthermore, when a predetermined time has passed, the inner cylinder of the injector is slowly brought down and the state of adherence of blood to the wall of the injector is examined. Then, the injector is gently laid horizontally and the flowability of blood is examined. In the Imai method, a watch glass having a diameter of 11 cm is sterilized and disinfected and a 0.1% solution of the sample in a physiological saline solution is dropped onto the watch glass. The watch glass is rotated in an inclined state so that the solution in the watch glass has a circular shape having a diameter of about 3.5 cm, and the watch glass is lightly wiped with gauze. Then, 0.3 ml of fresh whole blood is added into the watch glass and the watch glass is similarly rotated so that the blood in the watch glass has a circular shape having a diameter of 3.5 cm. The watch glass is covered with a lid. When a predetermined time has passed, the watch glass is washed two times by using 20 ml of water, and the dissolved portion is thrown away. Then, 5.0 ml of 37% formalin is added to the residue and the mixture is allowed to stand still for 5 minutes. The fixed blood thrombus is separated, washed sufficiently with 10 ml of water and dried, and the weight is measured. Also in this case, the experiment is carried out on a watch glass treated only with the physiological saline solution (blank). Each experiment is conducted 5 times with respect to each sample, and a mean value is calculated.

The present invention will now be described in detail with reference to the following Examples that by no means limit the scope of the invention.

EXAMPLE 1

This Example illustrates a process wherein sodium cellulose sulfate in which the value $<<F>>$ is in the range of $2.0<<<F>><2.6$ and the value $<<f_2>>$ is largest among the values $<<f_2>>$, $<<f_3>>$ and $<<f_6>>$ is prepared by using adsorbent cotton having the polymerization degree adjusted to 600 and an $SO_3/DMF$ (½ molar ratio) complex in an amount of 4 moles per mole of cellulose.

To 10.0 g of dry adsorbent cotton was added 10.0 ml of DMF which had been subjected to a dehydration treatment, and the adsorbent cotton was compressed for 10 minutes. Then, 56.0 g of an $SO_3/DMF$ (½ molar ratio) complex was added to the compressed adsorbent cotton, and the mixture was stirred under compression while maintaining the temperature at 25° C. When stirring was conducted for about 20 minutes, a highly viscous, brown, transparent product was obtained. Stirring was further conducted for 40 minutes, and the product was subjected to the substitution degree-adjusting treatment under conditions shown in Table 1 and was then neutralized with 2 N NaOH. An excessive amount of methanol as added to the obtained solution to cause precipitation. The precipitate was washed several times with 200 ml of a methanol/water (7/3 volume ratio) mixed liquid and was then dried. All the dry products obtained in this Example were brown. Each dry product was dissolved in water at a concentration of about 1 to about 2% and 10 g of diatomaceous earth for the filtration of beer was added to the solution, and the mixture was allowed to stand still for 20 minutes. The mixture was filtered by filter paper and the filtrate was precipitated with methanol to obtain a white precipitate. The precipitate was dried and dissolved in deionized water at a concentration of 2 g/dl, and the solution was dialyzed with deionized water. The dialysis was stopped when the specific electric conductivity of the dialyzate was $10^{-6}\Omega^{-1}$ cm$^{-1}$. Water was completely removed from the obtained solution by an evaporator to obtain pure white sodium cellulose sulfate. These cellulose sulfate salts thus obtained under various substitution degree-adjusting conditions were subjected to chemical analysis and $H^1$-NMR measurement in heavy water to determine values $<<F>>$, $<<f_2>>$, $<<f_3>>$ and $<<f_6>>$. The obtained results are shown in Table 1. Simultaneously, the limiting viscosity number $[\eta]$ was measured at 25° C. in 0.5 n $Na_2SO_4$ and the value a in the formula of $[\eta]=K_1\times Mw^a$ was calculated from the value $[\eta]$. The obtained results are shown in Table 1. Separately, two comparative products having a value $<<F>>$ larger than 2.6 were prepared in the same manner as described above except that the substitution degree-adjusting treatment was carried out below 0° C. and the neutralization was carried out at $-10°$ C.

The so obtained synthesis products 1 and 4 and comparative products 1 and 2 were separately dissolved in a physiological saline solution at a concentration of 0.1 g/dl, and the respective solutions were stored. At predetermined time intervals, the pH values and the coagulating property retention ratios were determined to obtain the results shown in Table 2. From the results shown in Table 2, it will readily be understood that the cellulose sulfate salt having a value $<<F>>$ smaller than 2.6 is much more excellent over the comparative product having a value $<<F>>$ larger than 2.6 in stability with the lapse of time.

TABLE 1

| | Substitution Degree-Adjusting Conditions and Substitution Degree Distributions of Obtained Sulfate Salts | | | | | |
|---|---|---|---|---|---|---|
| Item | Synthesis Product 1 | Synthesis Product 2 | Synthesis Product 3 | Synthesis Product 4 | Comparative Product 1 | Comparative Product 2 |
| Substitution Degree-Adjusting Conditions | | | | | | |
| Amount of Water (g/g of cellulose) | 5 | 3 | 1 | 5 | 5 | 5 |
| Temperature (°C.) | 10 | 25 | 45 | 60 | −5 | −15 |
| Time (minutes) | 10 | 15 | 15 | 10 | 3 | 3 |
| Substitution Degrees | | | | | | |
| $<<F>>$ | 2.58 | 2.32 | 2.13 | 2.02 | 2.65 | 2.92 |
| $<<f_2>>$ | 1.00 | 1.00 | 1.00 | 0.90 | 1.00 | 1.00 |
| $<<f_3>>$ | 0.92 | 0.64 | 0.62 | 0.80 | 0.92 | 0.92 |

TABLE 1-continued

Substitution Degree-Adjusting Conditions and Substitution Degree Distributions of Obtained Sulfate Salts

| Item | Synthesis Product 1 | Synthesis Product 2 | Synthesis Product 3 | Synthesis Product 4 | Comparative Product 1 | Comparative Product 2 |
|---|---|---|---|---|---|---|
| $<<f_6>>$ | 0.64 | 0.68 | 0.51 | 0.32 | 0.73 | 1.00 |
| $[\eta]$ (cm$^3$/g) | 220 | 202 | 270 | 230 | 410 | 405 |
| Value a in Formula of $[\eta] = K_1 \times Mw^a$ | 0.98 | 0.98 | 0.97 | 0.98 | 0.97 | 0.96 |

TABLE 2

Stabilities of Cellulose Sulfate Salt's Anti-Coagulating Property Retention Ratio (%) and pH Value

| Item | Synthesis Product 1 | Synthesis Product 4 | Comparative Product 1 | Comparative Product 2 |
|---|---|---|---|---|
| After 1 week | | | | |
| Retention ratio | 100 | 100 | 100 | 99 |
| pH Value | 5.7 | 5.73 | 5.65 | 5.30 |
| After 3 weeks | | | | |
| Retention ratio | 100 | 100 | 98 | 95 |
| pH Value | 5.42 | 5.42 | 5.30 | 5.10 |
| After 5 weeks | | | | |
| Retention ratio | 98 | 100 | 82 | 88 |
| pH Value | 5.10 | 5.30 | 4.98 | 4.95 |
| After 7 weeks | | | | |
| Retention ratio | 92 | 96 | 78 | 61 |
| pH Value | 5.08 | 5.10 | 4.97 | 4.10 |
| After 9 weeks | | | | |
| Retention ratio | 86 | 94 | 79 | 35 |
| pH Value | 4.72 | 5.05 | 4.95 | 3.95 |
| After 12 weeks | | | | |
| Retention ratio | 88 | 94 | 61 | 10 |
| pH Value | 4.78 | 5.05 | 4.30 | 3.32 |

EXAMPLE 2

This Example illustrates a process wherein sodium cellulose sulfate in which the value $<<F>>$ is in the range of $1.55 \leq <<F>> \leq 2.10$ and the value $<<f_2>>$ is largest among the values $<<f_2>>$, $<<f_3>>$ and $<<f_6>>$ is prepared by using microcrystalline cellulose having the polymerization degree adjusted to 220 (Avicel manufactured and supplied by Asahi Kasei Kogyo K.K.) and an SO$_3$/pyridine ($\frac{1}{2}$ molar ratio) complex in an amount of 3 moles per mole of cellulose.

To 30 g of dry Avicel was added 20 ml of purified pyridine to swell the Avicel, and 110 g of an SO$_3$/pyridine ($\frac{1}{2}$ molar ratio) complex was added and the mixture was vigorously stirred at room temperature. When stirring was conducted for about 10 to about 15 minutes, a highly viscous, brown, transparent product was obtained. Stirring was further conducted for 20 minutes, and the product was subjected to the substitution degree-adjusting treatment under conditions shown in Table 3 and was then neutralized with 6 N NaOH. An excessive amount of ethanol was added to the obtained solution to cause precipitation. The precipitate was sufficiently washed with an ethanol/water (8/2 volume ratio) mixed liquid to obtain a dark brown, crude cellulose sulfate salt. When the salt was dissolved in water, the solution was brown and had a strong smell of pyridine. The aqueous solution of the salt having the concentration adjusted to about 1% was passed at a rate of 10 ml/min through a layer of activated carbon packed in a cylindrical column having an inner diameter of 3 cm and a height of 5 cm. The effluent was substantially colorless and transparent and had no smell of pyridine. The solution was dialyzed in the same manner as described in Example 1 to obtain a cellulose sulfate salt shown in Table 3.

For comparison, a cellulose sulfate salt (comparative product 3) in which the value $<<f_2>>$ was small and was not largest among the values $<<f_2>>$, $<<f_3>>$ and $<<f_6>>$ was prepared under severer conditions.

Each of the so obtained synthesis products B 5 through 9 and comparative product 3 was excellent in stability with the lapse of time. When the synthesis product 9 and comparative product 3 which had substantially the same value $<<F>>$ but were different in the substitution degree distribution were compared with each other with respect to the anti-coagulating property (Lee-White method), it was seen that in the synthesis product 9, 60 minutes were required for initiation of the coagulation of blood, while in the comparative product 3, 21 minutes were required for initiation of the coagulation of blood.

TABLE 3

Substitution Degree-Adjusting Conditions and Substitution Degree Distributions of Obtained Sulfate Salts

| Item | Synthesis Product 5 | Synthesis Product 6 | Synthesis Product 7 | Synthesis Product 8 | Synthesis Product 9 | Comparative Product 3 |
|---|---|---|---|---|---|---|
| Substitution Degree-Adjusting Conditions | | | | | | |
| Amount of Water (g/g of cellulose) | 3 | 10 | 1 | 3 | 5 | 10 |
| Temperature (°C.) | 25 | 18 | 40 | 35 | 48 | 65 |
| Time (minutes) | 20 | 25 | 8 | 20 | 20 | 40 |
| Substitution Degrees | | | | | | |
| $<<F>>$ | 2.06 | 1.91 | 1.74 | 1.63 | 1.55 | 1.54 |
| $<<f_2>>$ | 1.00 | 1.00 | 0.92 | 0.98 | 0.96 | 0.52 |
| $<<f_3>>$ | 0.72 | 0.62 | 0.51 | 0.38 | 0.38 | 0.58 |
| $<<f_6>>$ | 0.34 | 0.28 | 0.33 | 0.27 | 0.21 | 0.44 |
| $[\eta]$ (cm$^3$/g) | 220 | 232 | 180 | 150 | 142 | 90 |
| Value a in Formula of $[\eta] = K_1 \times Mw^a$ | 0.98 | 0.98 | 0.98 | 0.96 | 0.97 | 0.89 |

EXAMPLE 3

This Example illustrates a process for preparing sodium cellulose sulfate excellent in the anti-coagulating property, which has a value $<<F>>$ smaller than 1.5 and a low degree of polymerization and is characterized by $[\eta]$ of 10 to 68 as measued at 25° C. in 0.5 N Na$_2$SO$_4$.

In 60 ml of DMSO (dimethylsulfoxide) was immersed 30 g of adsorbent cotton prepared by acid hydrolysis and enzymatic decomposition and having a polymerization degree of 45, and while the temperature was maintained at 5° C., a pre-formed $SO_3$/DMF ($\frac{1}{2}$ molar ratio) complex was added in an amount of 107.5 g (2.5 moles per mole of cellulose). The mixture was vigorously stirred at the above temperature for 20 to 40 minutes to obtain a yellow pasty semi-transparent liquid. The liquid was divided into three equal parts and 150 ml of water was added to each part. The three mixtures were maintained at $-5°$ C., 0° C. and 10° C., respectively, for 20 minutes, during which floating substances were removed by filtration. Each of the obtained transparent solutions was neutralized with 4 N NaOH at the above-mentioned temperature. In the same manner as described in Example 1, the solution was subjected to the adsorbent agent treatment and dialysis treatment. Thus, three kinds of cellulose sulfate salts were obtained. The anti-coagulating properties of the so obtained sodium cellulose sulfates (synthesis products 10, 11 and 12) and the products obtained in Examples 1 and 2 (synthesis products 1, 4, 6 and 9) were tested according to the Imai method. For comparison, heparin was similarly tested and the blank test was conducted without using any anti-coagulant. The obtained results are shown in Table 4.

than 0.01% by weight and the pH value was 6.2 to 7.0. Since amides or amines are pyogenic substances, it is preferred that the nitrogen content be lower than 0.01% by weight.

EXAMPLE 4

This Example illustrates the preparation of cellulose sulfate salts, other than sodium cellulose sulfate, and their anti-coagulating properties.

In 200 ml of a 5% aqueous solution of each of calcium chloride, potassium chloride and magnesium chloride was dissolved 2 g of sodium cellulose sulfate (synthesis product 3) obtained in Example 1. When potassium chloride was used, the solution gelled. Therefore, in this case, the solution was maintained at 70° C. for preventing gelation. Each solution was allowed to stand still overnight and methanol was added to cause precipitation. The precipitate was dissolved in water again and dialysis was carried out in the same manner as described in Example 1. The solvent was removed and the residue was dried to obtain a white powder. The obtained results are shown in Table 5. The obtaind cellulose sulfate salt was dissolved in a physiological saline solution at a concentration of 0.01% (under heating, in the case of the potassium salt), and the amount of blood coagulum

TABLE 4

| | Anti-Coagulating Properties of Sodium Cellulose Sulfates | | | | | | | | |
|---|---|---|---|---|---|---|---|---|---|
| Item | Synthesis Product 10 | Synthesis Product 11 | Synthesis Product 12 | Synthesis Product 1 | Synthesis Product 4 | Synthesis Product 6 | Synthesis Product 9 | Heparin | Blank |
| Substitution Degrees | | | | | | | | | |
| $<<F>>$ | 0.82 | 1.18 | 1.38 | 2.58 | 2.02 | 1.74 | 1.55 | — | — |
| $<<f_2>>$ | 0.35 | 0.72 | 0.88 | 1.00 | 0.90 | 0.92 | 0.96 | — | — |
| $<<f_3>>$ | 0.30 | 0.33 | 0.38 | 0.92 | 0.80 | 0.51 | 0.38 | — | — |
| $<<f_6>>$ | 0.07 | 0.13 | 0.12 | 0.64 | 0.32 | 0.33 | 0.21 | — | — |
| $[\eta]$ (cm$^3$/g) | 12 | 20 | 67 | 320 | 230 | 232 | 142 | — | — |
| Value a in Formula of $[\eta] = K_1 \times M_w^a$ | 0.97 | 0.98 | 0.98 | 0.98 | 0.98 | 0.98 | 0.97 | — | — |
| Fixed thrombus (mg) | | | | | | | | | |
| After 10 minutes | 14.6 | 6.2 | 6.4 | 3.2 | 6.0 | 6.8 | 6.2 | 3.8 | 62.5 |
| After 30 minutes | 28.6 | 14.6 | 18.8 | 3.8 | 10.0 | 7.8 | 10.8 | 5.4 | 84.8 |
| After 50 minutes | 32.0 | 25.4 | 20.4 | 14.2 | 18.0 | 12.5 | 10.8 | 15.1 | — |
| After 80 minutes | 39.3 | 29.8 | 28.8 | 16.2 | 24.0 | 18.5 | 17.8 | 16.1 | — |
| After 120 minutes | 49.6 | 40.8 | 41.0 | 20.8 | 24.0 | 32.6 | 29.8 | 31.8 | 113.8 |

As is seen from the results shown in Table 4, although the cellulose sulfate salts prepared in this Example have a relatively small value $<<F>>$ of from 0.8 to 1.38, they have an anti-coagulating property comparable to those of cellulose sulfate salts having a high substitution degree and heparin. Moreover, as will be estimated from the results shown in Table 4, a product having a value $<<F>>$ smaller than 0.8 cannot be used appropriately as an anti-coagulant because the anti-coagulating property at the initial stage is insufficient. When the nitrogen content and the pH value of a 1% solution in pure water were measured with respect to each cellulose sulfate salt prior to the anti-coagulating property test, it was found that the nitrogen content was lower was measured at predetermined intervals according to the Imai method. The starting sodium salt and heparin were similarly tested, and the blank test was carried out without using any anti-coagulant. The obtained results are shown in Table 5.

TABLE 5

| | Anti-Coagulating Properties of Various Cellulose Sulfate Salts | | | | | |
|---|---|---|---|---|---|---|
| Item | Synthesis Product 2 (Na Salt) | K Salt | Mg Salt | Ca salt | Heparin | Blank |
| $<<F>>$ | 2.13 | 2.12 | 2.12 | 2.12 | | |
| Fixed thrombus (mg) | | | | | | |
| After 10 minutes | 3.4 | 3.6 | 3.9 | 4.1 | 3.8 | 62.5 |
| After 30 minutes | 4.2 | 5.3 | 5.2 | 6.3 | 5.4 | 84.8 |
| After 50 minutes | 13.8 | 18.0 | 17.3 | 7.4 | 15.1 | — |
| After 80 minutes | 16.4 | 21.0 | 20.8 | 16.3 | 16.1 | — |
| After 120 minutes | 21.0 | 25.5 | 29.8 | 26.4 | 31.8 | 113.8 |

From the results shown in Table 5, it is seen that the cellulose sulfate salts prepared in this Example are slightly inferior to the corresponding sodium salt in the anti-coagulating property but they are superior to heparin.

EXAMPLE 5

This Example illustrates that the cellulose sulfate salt obtained by the adsorbent treatment in the process of the present invention has a high purity.

In 100 ml of pure water was dissolved 1 g of the brown crude sodium cellulose sulfate (synthesis product 2) obtained in Example 2, and 0.5 g of an adsorbent shown in Table 6 was added to the solution. The mixture was allowed to stand still for 1 hour, filtered and precipitated with methanol. The precipitate was washed with 200 ml of a water/methanol (3/7 volume ratio) mixed liquid and dried. The nitrogen content in the obtained cellulose sulfate was determined by a CHN recorder. Separately, 1 g of the starting brown crude cellulose sulfate salt was dissolved in 100 ml of pure water and precipitated with methanol. The dissolution and precipitation treatments were repeated three times. The nitrogen content in the obtained product was similarly determined (comparison). The obtained results are shown in Table 6. Furthermore, each product was subjected to the pyrogenic and UV absorbing property tests according to the methods of the Japanese Pharmacopoeia. In Table 6, mark "A" indicates that the sample passed the test, mark "C" indicates that the sample did not pass the test, and mark "B" indicates that the sample was on the borderline.

TABLE 6

Nitrogen Contents and Pyrogenic Properties of Adsorbent-Treated Cellulose Sulfate Salts

| Adsorbent | Nirogen Content (% by weight) | Pyrogenic and UV Absorbing Property Tests |
|---|---|---|
| Diatomaceous earth | 0.010 | A |
| Active carbon | 0.005 | A |
| Activated alumina | 0.005 | A |
| Bentonite | 0.040 | A-B |
| Magnesium silicate | 0.082 | B |
| Zirconyl hydroxide | 0.018 | A |
| Silica gel | 0.024 | B |
| Comparison | 0.29 | C |

From the results shown in Table 6, it will readily be understood that a cellulose sulfate salt substantially free of impurities can be obtained by a very simple step in the present invention.

We claim:

1. A cellulose sulfate salt having a heparinic action, which satisfies the requirements of $0.8 \leq <<F>> \leq 2.6$, $<<f_2>> \geq <<f_3>>$ and $<<f_2>> \geq <<f_6>>$ wherein $<<f_2>>$, $<<f_3>>$ and $<<f_6>>$ stand for probability of substitution of atoms H in OH groups bonded to the $C_2$, $C_3$ and $C_6$ positions of the glucopyranose ring unit by sulfuric acid radicals, respectively, and $<<F>>$ stands for the total substitution degree which is the sum of $<<f_2>>$, $<<f_3>>$ and $<<f_6>>$.

2. A cellulose sulfate salt as set forth in claim 1, wherein the total substitution degree $<<F>>$ is in the range of $1.5 < <<F>> < 2.4$.

3. A cellulose sulfate salt as set forth in claim 1, wherein the limiting viscosity number $[\eta]$ of a sodium salt thereof is in the range of from 10 to 430 cm$^3$/g as determined at 25° in a 0.5 N sodium sulfate solution and the index a defined by the following two formulae of the limiting viscosity number relative to the weight average molecular weight (Mw) and the number average molecular weight (Mn) is not less than 0.9:

$$[\eta] = K_1 \times Mw^a$$

wherein $K_1$ is a constant, and $$[\eta] = K_2 \times Mn^a$$

wherein $K_2$ is a constant.

4. A cellulose sulfate salt as set forth in claim 1, which is a salt of a metal selected from the group consisting of sodium, calcium and magnesium.

5. A cellulose sulfate salt as set forth in claim 1, wherein the nitrogen content is not more than 0.01% by weight.

6. A cellulose sulfate salt as set forth in claim 1, wherein a 5% (weight/volume) aqueous solution thereof has a pH value of from 5.3 to 7 and, when said aqueous solution is dialyzed with pure water, the specific electric conductivity of the dialyzate is not higher than $10^{-5} \Omega^{-1}$ cm$^{-1}$.

7. A process for the preparation of a cellulose sulfate salt as set forth in claim 1, which comprises reacting a cellulose having a crystal form I with an SO$_3$/amine complex or a SO$_3$/amide complex in an amount of 2 to 4 mole equivalents per glucose unit of the cellulose at a temperature of from −10° C. to 40° C. to form a gelatinous product containing a cellulose sulfate salt having fixed values of $<<f_2>>$ and $<<f_3>>$; adding water to the gelatinuous product in an amount 0.1 to 5 times the amount of the starting cellulose used for the reaction; treating the mixture at a temperature of not higher than 60° C. for 3 to 45 minutes to relatively reduce the values of $<<f_6>>$ and $<<f_3>>$ among the values of $<<f_2>>$, $<<f_3>>$ and $<<f_6>>$; neutralizing, precipitating and drying the so obtained crude cellulose sulfate salt; dissolving the crude cellulose sulfate salt in water again; treating the solution with an adsorbent; and subjecting the treated cellulose sulfate salt to precipitation, drying, re-dissolution, dialysis, precipitation and then drying.

8. A process according to claim 7, wherein a sulfate salt of a metal selected from the group consisting of sodium, calcium and magnesium is formed.

9. A process according to claim 7, wherein the aqueous solution of the crude cellulose sulfate salt is treated with the adsorbent to an extent such that the nitrogen content in the finally obtained cellulose sulfate salt is not more than 0.01% by weight.

10. A process according to claim 7, wherein the aqueous solution of the crude cellulose sulfate salt is treated with the adsorbent to an extent such that the treated cellulose sulfate salt exhibits a pH value of from 5.3 to 7.0 as determined in a 5% (weight/volume) aqueous solution thereof.

11. A process according to claim 7, wherein the dialysis of the cellulose sulfate salt is carried out to an extent such that, when the resulting cellulose sulfate salt is dissolved in deionized water at a concentration of 5 g/dl, the specific electric conductivity of deionized water used as the dialyzing liquid becomes not higher than $10^{-5} \Omega^{-1}$ cm$^{-1}$.

* * * * *